United States Patent [19]

Willis et al.

[11] 4,339,593
[45] Jul. 13, 1982

[54] PROCESS FOR THE MANUFACTURE OF 3,6-DIALKYL RESORCYLIC ACID ESTERS

[75] Inventors: Brian J. Willis, Ramsey; David I. Lerner, Teaneck, both of N.J.; Derek H. R. Barton, Gif-sur-Yvette, France

[73] Assignee: Fritzsche Dodge & Olcott Inc., New York, N.Y.

[21] Appl. No.: 216,901

[22] Filed: Dec. 16, 1980

[51] Int. Cl.³ ............................................. C07C 69/76
[52] U.S. Cl. ..................................................... 560/70
[58] Field of Search ......................................... 560/70

[56] References Cited

U.S. PATENT DOCUMENTS

| | | | |
|---|---|---|---|
| 2,849,480 | 8/1958 | Kreuchunas | 560/70 |
| 3,634,491 | 1/1972 | Grossman | 560/70 |
| 3,701,801 | 10/1972 | Grossman | 560/70 |
| 3,790,636 | 2/1974 | Brossi | 560/70 |
| 3,824,272 | 7/1974 | Brossi | 560/70 |
| 3,944,596 | 3/1976 | Cohen | 560/70 |

Primary Examiner—Paul J. Killos

Attorney, Agent, or Firm—Cooper, Dunham, Clark, Griffin & Moran

[57] ABSTRACT

Dialkyl-substituted β-resorcylic acid esters having the structure:

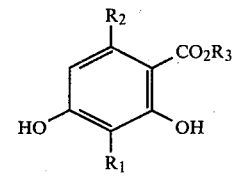

wherein each of $R_1$, $R_2$, and $R_3$ is lower alkyl may be readily prepared by reacting the corresponding dihydroresorcylic acid esters with sulfuryl chloride. These compounds, particularly, methyl 3,6-dimethyl-resorcylate and methyl 3-ethyl-6-methyl-resorcylate, have oakmoss-like odors rendering them valuable as perfume ingredients.

11 Claims, No Drawings

PROCESS FOR THE MANUFACTURE OF 3,6-DIALKYL RESORCYLIC ACID ESTERS

BACKGROUND OF THE INVENTION

Natural oakmoss is of importance to the fragrance industry. It is used in high grade perfume compositions such as lavender, chypre, and fougere. Unfortunately, the supply of natural oakmoss is limited. As a result, synthetic substitutes have been sought. Specifically, methyl 3,6-dimethyl-resorcylate and methyl 3-ethyl-6-methyl-resorcylate are important synthetics having oakmoss-like odors.

Several synthetic methods are known for preparing dialkyl resorcylic acid esters from the corresponding dihydroresorcylic acid esters. The dihydroresorcylic esters may be obtained by condensing malonic acid esters with α,β-unsaturated ketones. [U. Steiner and B. Willhalm, Helv. Chim. Acta, 35, 1752 (1952)]. The dihydroresorcylic acid esters may be aromatized by known methods. For example, a method reported by A. Sonn [Ber. Deut. Chem. Ges. 62B, 3012 (1929)] uses a palladium catalyst for aromatization. Another method employing chlorine gas is disclosed in Grossman, J. D. et al., U.S. Pat. No. 3,634,491 (1972). Aromatization via a bromination, dehalogenation sequence has also been reported. [Kulka, K. et al., U.S. Pat. No. 3,884,843 (1975), assigned to Fritzsche Dodge & Olcott Inc., New York, N.Y., the assignee herein.] Finally, Klein, E. et al., U.S. Pat. No. 4,142,053 (1979) discloses the aromatization of dihydro-β-resorcylic acid esters with sulfuric acid and acetic anhydride, followed by saponification of the resulting diacetates.

Thus, there are a number of known methods for preparing resorcylic acid esters. However, there is no teaching or suggestion in the prior art of converting dihydroresorcylic acid esters to 3,6-dialkyl resorcylic acid esters according to the low cost, efficient process provided by this invention.

SUMMARY OF THE INVENTION

Specifically, this invention provides a process for converting dihydroresorcylic acid esters having the general structure:

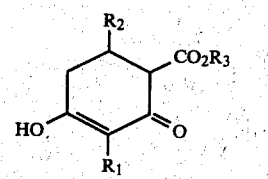

I wherein each of $R_1$, $R_2$, and $R_3$ is $C_1$ to $C_3$ alkyl to 3,6-dialkyl resorcylic acid esters having the structure:

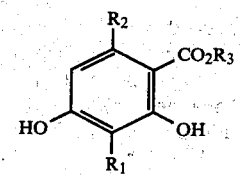

II wherein each of $R_1$, $R_2$, and $R_3$ is as defined previously.

The process involves treating a dihydroresorcylic acid ester (I) with sulfuryl chloride in the presence of a suitable solvent, preferably a non-hydroxylic solvent, and permits preparation of a dialkyl-substituted resorcylic acid ester (II) in a simple, one-pot procedure which is both efficient and economical.

DETAILED DESCRIPTION OF THE INVENTION

Depending upon the 3,6-dialkyl resorcylic acid ester required, the appropriate dihydroresorcylic acid ester (I) may be suspended in a suitable solvent such as benzene or chloroform, or may preferably be dissolved in a solvent such as dimethylformamide, 1-methyl-2-pyrrolidinone, dimethylacetamide, or pyridine; or a mixed solvent system such as dimethylformamide/pyridine. The dihydroresorcylic acid ester is then treated with sulfuryl chloride at a suitable temperature in the range from about −5° to about 100° C., preferably under an inert atmosphere. Optimum yields of dialkyl-substituted resorcylic acid esters are obtained when addition of sulfuryl chloride is carried out at temperatures between about −5° and about 25° C., and the reaction temperature is raised to a temperature from about 25° to 100° C. when addition of sulfuryl chloride is complete. Although the amounts of reactants employed may vary, it is desirable that the amount of sulfuryl chloride used in the reaction be in the range from about 0.5 to about 2.0 equivalents. Preferably, the reaction with sulfuryl chloride is carried out with a stoichiometric amount of the reagent, since the use of less than one equivalent of sulfuryl chloride results in production of mixtures containing unreacted dihydroresorcylic acid esters and the use of more than one equivalent of sulfuryl chloride results in the production of by-products which complicate the purification of the desired dialkyl-substituted resorcylic acid esters.

The work-up procedure utilized to recover the reaction product depends upon the solvent employed in the reaction. For example, if the reaction is carried out in benzene or chloroform, it is only necessary to wash the solution with aqueous sodium bicarbonate solution, evaporate the solvent, and recrystallize the crude dialkyl-substituted resorcylic acid ester (II). With solvents such as dimethylformamide, 1-methyl-2-pyrrolidinone, dimethylacetamide, pyridine, or mixed solvent systems such as benzene/pyridine, or dimethylformamide/pyridine, aqueous or acidic work-up is preferred. The product is then extracted from the aqueous mixture with a solvent such as ethyl acetate. The resulting extract is then washed with aqueous sodium bicarbonate solution, the solvent evaporated, and the crude product purified by standard techniques.

The following examples are set forth to more fully illustrate the practices of the invention, but are in no way meant to limit the scope thereof.

EXAMPLE 1

METHYL 3,6-DIMETHYL-RESORCYLATE

In a 5 L. round-bottom flask fitted with a reflux condenser, stirrer, thermometer, and addition funnel, are placed methyl 3,6-dimethyl-dihydroresorcylate (336.6 g, 1.70 mol) dissolved in dimethylformamide (1 L.). The solution is cooled to 5° C. under nitrogen, and sulfuryl chloride (229.5 g, 1.70 mol) is added dropwise, with stirring, while maintaining the temperature at 5°–10° C. The reaction mixture is then stirred at 10° C. for an additional 1 h, and at 25° C. for 4 h. The solution is then cooled to 5° C., and pyridine (403.4 g, 5.10 mol) is added dropwise, with stirring, at a temperature of 5°–10° C.

The stirred solution is heated at 60°–65° C. for 7 h, cooled to 5° C., and acidified with 6 N hydrochloric acid (900 ml.). The mixture is extracted with ethyl acetate (1 L.), and the layers are separated. The aqueous layer is reextracted with ethyl acetate (500 ml), and the combined organic layer is neutralized by washing twice with saturated sodium bicarbonate solution (600 ml each time) and once with water (500 ml). After drying over anhydrous sodium sulfate, the solvent is distilled at reduced pressure to yield the crude methyl 3,6-dimethyl-resorcylate. The product is purified by dissolving it in hot methanol (800 ml) and slowly adding, with stirring, distilled water (300 ml) to the warm methanolic solution to effect precipitation of the product. The mixture is cooled to 0° C. and the precipitate collected, washed thoroughly with water, and dried, yielding 283 g (85%) methyl 3,6-dimethyl-resorcylate, Mp. 142°–143° C. The product exhibits the expected spectral data.

EXAMPLE 2

METHYL 3-ETHYL-6-METHYL-RESORCYLATE

Employing procedures and materials similar to those described in Example 1, except that methyl 3-ethyl-6-methyl-dihydroresorcylate is substituted for methyl 3,6-dimethyl-dihydroresorcylate, there is obtained the desired product, methyl 3-ethyl-6-methyl-resorcylate. Yield (79%), Mp. 105°–106° C. The product exhibits the expected spectral data.

EXAMPLE 3

METHYL 3,6-DIMETHYL-RESORCYLATE

In a 200 ml round-bottom flask fitted with a reflux condenser, stirrer, thermometer, and septum, are placed methyl 3,6-dimethyl-dihydroresorcylate (1.98 g, 0.01 mol) suspended in benzene (75 ml). The mixture is cooled to 5° C. under nitrogen, and sulfuryl chloride (1.35 g, 0.01 mol) is added dropwise, with stirring, while maintaining the temperature at 5°–10° C. The reaction mixture is then stirred at 10° C. for an additional 1 h, at 25° C. for 1 h, and then heated at 60° C. for 8 h. The resulting solution is cooled to 25° C., washed twice with saturated sodium bicarbonate solution (50 ml each time), and once with water (50 ml). The solvent is distilled at reduced pressure to give 1.47 g (75% yield) of crude methyl 3,6-dimethyl-resorcylate. This product requires recrystallization to provide material of suitable fragrance quality.

As will be obvious to one skilled in the art, many modifications, variations, and alterations can be made in the practices of this invention without departing from the spirit and scope thereof as set forth in the claims which follow.

What is claimed is:

1. A process for preparing a 3,6-dialkyl resorcylic acid ester having the structure:

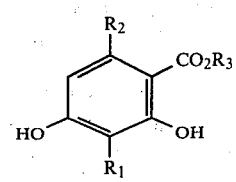

wherein each of $R_1$, $R_2$, and $R_3$ is $C_1$ to $C_3$ alkyl, which comprises treating a dihydroresorcylic acid ester having the general structure:

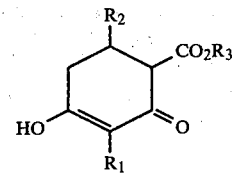

wherein each of $R_1$, $R_2$, and $R_3$ is $C_1$ to $C_3$ alkyl, with sulfuryl chloride in the presence of a suitable solvent, said treatment being carried out at a temperature in the range from about −5° to about 100° C., and recovering the resulting 3,6-dialkyl resorcylic acid ester.

2. A process in accordance with claim 1 wherein the amount of sulfuryl chloride is in the range from about 0.5 to about 2.0 equivalents.

3. A process in accordance with claim 2 wherein the amounts of dihydroresorcylic acid ester and of sulfuryl chloride are about stoichiometric.

4. A process in accordance with claim 1 wherein said suitable solvent is benzene or chloroform and said dihydroresorcylic acid ester is present as a suspension therein.

5. A process in accordance with claim 1 wherein said suitable solvent is dimethylformamide, 1-methyl-2-pyrrolidinone, dimethylacetamide, pyridine, or a benzene/pyridine or dimethylformamide/pyridine mixed solvent system and said dihydroresorcylic acid ester is dissolved therein.

6. A process in accordance with claim 1 wherein said temperature is in the range from about −5° to about 25° C.

7. A process in accordance with claim 1 wherein each of $R_1$, $R_2$, and $R_3$ is methyl and said suitable solvent is dimethylformamide/pyridine.

8. A process in accordance with claim 1 wherein $R_1$ is ethyl, each of $R_2$ and $R_3$ is methyl, and said suitable solvent is dimethylformamide.

9. A process in accordance with claim 1 wherein each of $R_1$, $R_2$, and $R_3$ is methyl and said suitable solvent is benzene.

10. A process in accordance with claim 1 wherein each of $R_1$, $R_2$, and $R_3$ is methyl and said suitable solvent is dimethylformamide.

11. A process in accordance with claim 1 wherein said treatment is carried out at a temperature in the range from about −5° to about 25° C. during sulfuryl chloride addition and at a temperature from about 25° to about 100° C. when addition is complete.

* * * * *